United States Patent [19]

Tanaka et al.

[11] Patent Number: 4,964,616

[45] Date of Patent: Oct. 23, 1990

[54] TRICYCLIC CYCLOHEXENYL CYCLOHEXANE DERIVATIVE

[75] Inventors: Yasuyuki Tanaka; Kiyofumi Takeuchi, both of Tokyo; Yuji Tamura, Saitama, all of Japan

[73] Assignee: Dainippon Ink and Chemicals, Inc., Tokyo, Japan

[21] Appl. No.: 381,357

[22] Filed: Jul. 18, 1989

[30] Foreign Application Priority Data

Jul. 19, 1988 [JP] Japan .................................. 63-178086

[51] Int. Cl.$^5$ ...................... C09K 19/30; C07C 41/00
[52] U.S. Cl. ............................ 252/299.63; 252/299.6; 568/664
[58] Field of Search ............. 252/299.5, 299.6, 299.63; 350/350 R; 568/664

[56] References Cited

U.S. PATENT DOCUMENTS

| | | | |
|---|---|---|---|
| 4,422,951 | 12/1983 | Sugimori et al. | 252/299.63 |
| 4,477,369 | 10/1984 | Sugimori et al. | 252/299.63 |
| 4,654,421 | 3/1987 | Tanaka et al. | 252/299.63 |
| 4,663,073 | 5/1987 | Sucrow et al. | 252/299.63 |
| 4,698,177 | 10/1987 | Tanaka et al. | 252/299.63 |
| 4,846,998 | 7/1989 | Pohl et al. | 252/299.63 |

FOREIGN PATENT DOCUMENTS

| | | | |
|---|---|---|---|
| 3510434 | 9/1986 | Fed. Rep. of Germany | 252/299.63 |
| 62-87533 | 4/1987 | Japan | 252/299.63 |

*Primary Examiner*—John S. Maples
*Assistant Examiner*—Richard Treanor
*Attorney, Agent, or Firm*—Armstrong, Nikaido, Marmelstein, Kubovcik & Murray

[57] ABSTRACT

A tricyclic cyclohexenyl cyclohexane derivative is disclosed. This compound is capable of lowering the Δn value of mixed liquid crystals, which have been obtained by adding said compound to nematic liquid crystals widely used as matrix liquid crystals, and elevating the N-I point thereof. Thus it is highly useful in the production of liquid crystal display cells.

12 Claims, No Drawings

TRICYCLIC CYCLOHEXENYL CYCLOHEXANE DERIVATIVE

FIELD OF THE INVENTION

This invention relates to a cyclohexenyl cyclohexane derivative useful as an electrooptical display material.

BACKGROUND OF THE INVENTION

Typical examples of liquid crystal display cells include a field effect mode cell proposed by M. Schadt et al. (*APPLIED PHYSICS LETTERS*, 18, 127–128 (1971)), a dynamic scattering mode cell proposed by G. H. Heilmeier et al. (*PROCEEDING OF THE I.E.E.E.*, 56, 1162–1171 (1968)) and a guest/host mode cell proposed by G. H. Heilmeier et al. (*APPLIED PHYSICS LETTERS*, 13, 91 (1968)) or D. L. White et al. (*JOURNAL OF APPLIED PHYSICS*, 45, 4718 (1974)).

Among these liquid crystal display cells, TN mode cells, which belong to the field effect mode cells, are majorly used at present. In the case of the TN mode cells, it is required to set the product of the optical anisotopy (Δn) of the liquid crystal material in the cell and the thickness (d; μm) of the cell to a definite value in order to achieve good cell appearance, as indicated by G. Bauer (*Mol. Cryst. Liq. Cryst.*, 63, 45 (1981)). A liquid crystal display cell used in practice has a Δn·d value of either 0.5, 1.0, 1.6 or 2.2. Generally speaking, the visual properties of a liquid crystal display cell can be improved by setting the Δn·d value to 0.5. On the other hand, the frontal contrast thereof can be improved by setting the Δn·d value to 1.0, 1.6 or 2.2. Therefore it is generally recommended to set the Δn d value of a liquid crystal display cell to 0.5, when it is regarded as important to achieve excellent visual properties from any direction. On the other hand, the Δn·d value thereof may be preferably set to 0.1, 1.6 or 2.2 in order to obtain a clear frontal contrast.

On the other hand, the thickness of a liquid crystal layer in a practially used liquid crystal display cell is commonly set to a definite value within a limited range of 6 to 10 μm. Thus a liquid crystal material having a low Δn value is required in order to set the Δn·d value to 0.5. In contrast thereto, a liquid crystal material having a high Δn value is required in order to set the Δn·d value to 1.0, 1.6 or 2.2. Namely, either a liquid crystal material having a low Δn value or one having a high Δn value is required depending on the desired display properties.

On the other hand, most of practically available liquid crystal materials are prepared by mixing several or more components selected from among compounds showing a nematic phase at around room temperature and those showing a nematic phase at a temperature range higher than room temperature. Most of these mixed liquid crystals practially employed today are required to show a nematic phase over the whole temperature range of at least −30° to +65° C. Therefore liquid crystal materials showing a nematic phase at around room temperature or higher are needed.

SUMMARY OF THE INVENTION

It is an object of the present invention to provide a novel compound capable of lowering the n value of mixed liquid crystals, which have been obtained by adding said compound to a nematic liquid crystals widely used in practice as matrix liquid crystals, and elevating the nematic-to-isotropic transition temperature (N-I point), namely, the upper limit of the tempeature range wherein said mixed liquid crystals show a nematic phase.

In order to achieve the above mentioned object, the present invention provides a compound represented by the general formula (I):

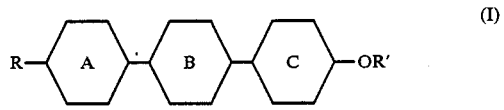

wherein R represents a straight-chain alkyl group having 1 to 9 carbon atoms; R' represents a straight-chain alkyl group having 1 to 9 carbon atoms or a trans-crotyl group; one of the rings

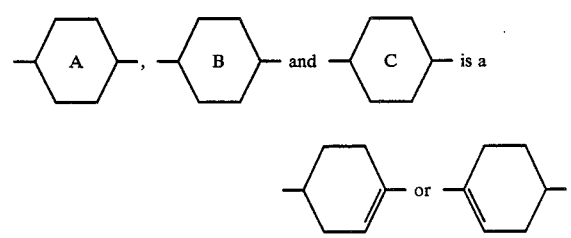

ring while other two rings are each a

ring; and the cyclohexane rings are arranged at a transconfiguration.

DETAILED DESCRIPTION OF THE INVENTION

The compound (I) of the present invention may be prepared by, for example, the following process (1), (2) or (3). Preparation process (1):

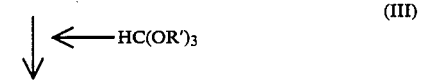

wherein R and R' are as defined above.

A compound represented by the formula (II) is reacted with a trialkyl orthoformate in the presence of a strongly acidic catalyst such as p-toluenesulfonic acid monohydrate. Then the temperature is slowly lowered under reduced pressure to thereby remove the alkanol and alkyl formate thus formed. Thus the compound (I-a) of the present invention is prepared.

4,964,616
3
Preparation process (2):
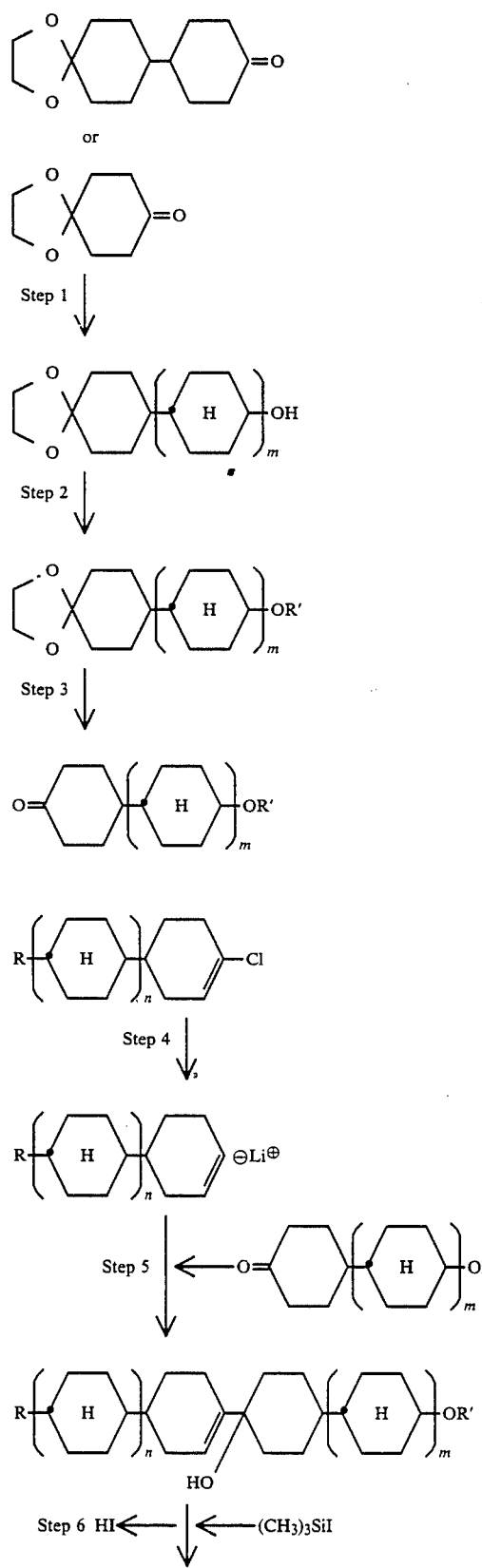
4
-continued
Preparation process (2):
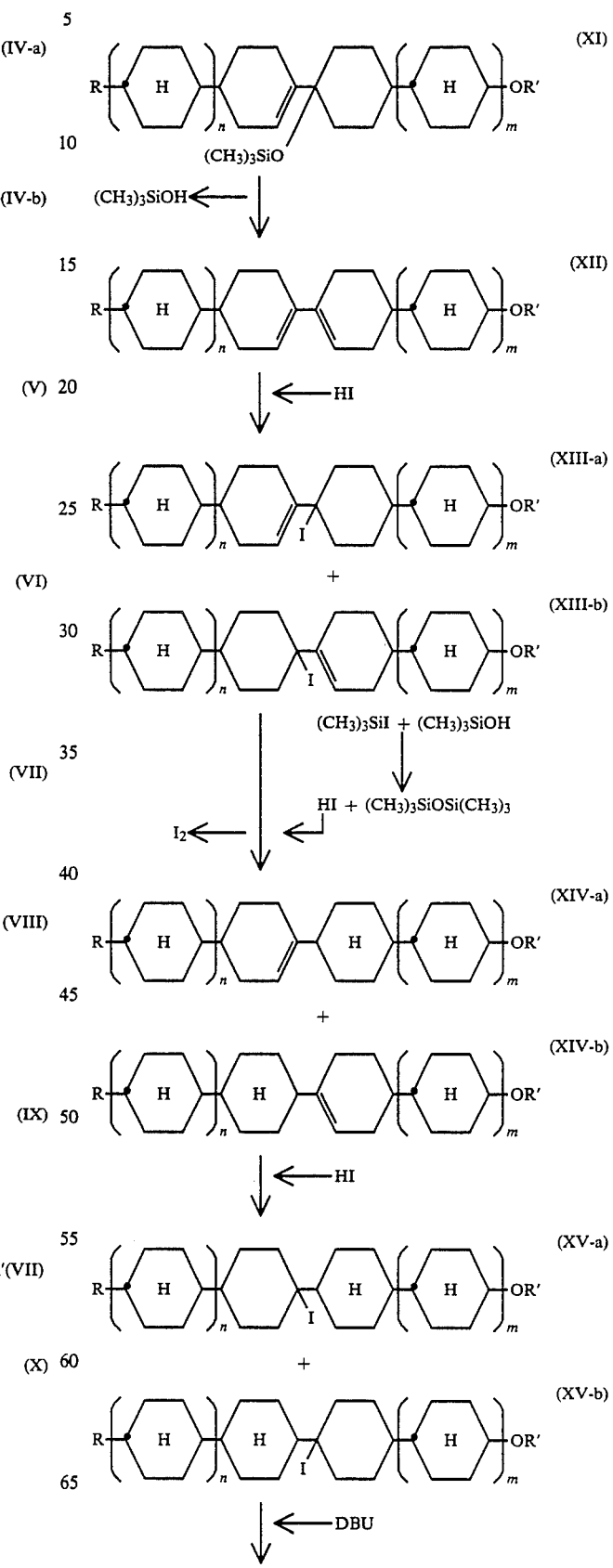

-continued
Preparation process (2):

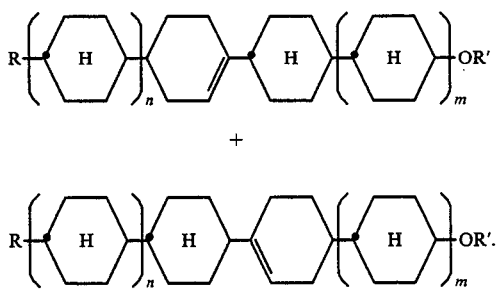

wherein R and R' are as defined above; and m and n represents each 0 or 1, provided that n=1 when m=0 and m=1 when n=0.

Step 1:
A compound represented by the formula (IV-a) or (IV-b) is reduced with sodium borohydride in a solvent mixture comprising an ether solvent such as tetrahydrofuran (THF) and an alcohol solvent such as ethanol solvent to thereby give a compound represented by the formula (V).

Step 2:
The compound (V) is reacted with an alkyl iodide in absolute THF in the presence of a sodium hydride to thereby give a compound of the formla (VI).

Step 3:
The compound (VI) is hydrolyzed by reacting with an acidic aqueous solution such as dilute sulfuric acid in an inert solvent such as toluene at the reflux temperature to thereby give a compound of the formula (VII).

Step 4:
The compound (VIII) is reacted with lithium in absolute diethyl ether at the reflux temperature for 4 to 7 hours to thereby give a compound of the formula (IX).

Step 5:
The compound (VII) is dissolved in an ether solvent such as absolute diethyl ether. The solution thus obtained is added to the solution of the compound (IX) in absolute diethyl ether, which is obtained above, at −15° to 0° C. Then the obtained mixture is allowed to react at 0° to 25° C. for 30 minutes. The reaction mixture is hydrolyzed by adding into cold water and the reaction product thus obtained is extracted with toluene. The extract is washed with water and dried. After distilling off the solvent from the extract, a compound of the formula (X) is obtained.

Step 6:
The compound (X) is dissolved in toluene. The solution thus obtained is added to a solution of iodotrimethylsilane in acetonitrile which have been prepared from chlorotrimethylsilane and sodium iodide in acetonitrile. Then the obtained mixture is reacted at 5° to 10° C. for 30 minutes to 1 hour. Thus a reaction mixture comprising compounds of the formulae (XIV-a), (XIV-b), (XV-a) and (XV-b) is prepared from the compound (X) via compounds of the formulae (XI), (XII), (XIII-a) and (XIII-b).

To the reaction mixture thus obtained, is added a base such as 1,8-diazo-bicyclo(5,4,0)undecene-7 (DBU). The resulting mixture is allowed to react at 5° to 30° C. for 3 to 5 hours and then at the reflux temperature for 1 hour. Then water is added to the reaction mixture and the reaction product is extracted therefrom with toluene. The extract is successively washed with a dilute solution of hydrochloric acid, a saturated aqueous solution of acidic sodium sulfite, a saturated aqueous solution of sodium hydrogencarbonate and a saturated aqueous solution of common salt. After drying, the solvent is distilled off from the extract.

The crude reaction product thus obtained is purified by chromatography on silica gel and recrystallized from ethanol. Thus a mixture of the compounds (I-b) and (I-c) of the present invention is obtained.

Next, each of the compounds (I-b) and (I-c) is separated from the above mentioned mixture by high performance liquid chromatography. Each compound thus isolated is then recrystallized from ethanol. Thus the compounds (I-b) and (I-c) of the present invention are obtained.

Preparation process (3):

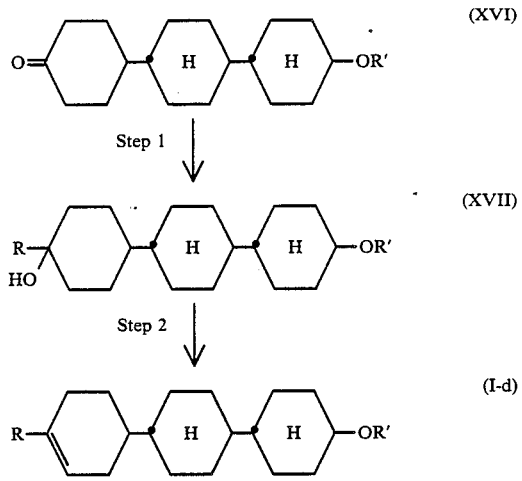

wherein R and R' are as defined above.

Step 1:
A compound of the formula (XVI) is reacted with a n-alkylmagnesium bromide in absolute THF to thereby give a compound of the formula (XVII).

Step 2:
The compound (XVII) is dehydrated by reacting in toluene in the presence of an acidic catalyst such as p-toluenesulfonic acid monohydride at the reflux temperature to thereby give a compound of the formula (I-d) of the present invention.

Table 1 shows the transition temperatures of typical compounds (I) of the present invention thus obtained.

TABLE 1

| No. | R | A | B | C | R' | Transition temperature (°C.) |
|---|---|---|---|---|---|---|
| 1 | n-C₃H₇— | cyclohexene | cyclohexane (H) | cyclohexane (H) | —C₂H₅ | 174 (S ⇌ I) |
| 2 | n-C₃H₇— | cyclohexane (H) | cyclohexene | cyclohexane (H) | —C₂H₅ | 158 (S ⇌ I) |
| 3 | n-C₃H₇— | cyclohexane (H) | cyclohexene | cyclohexane (H) | —C₂H₅ | 156 (S ⇌ I) |
| 4 | n-C₃H₇— | cyclohexane (H) | cyclohexane (H) | cyclohexene | —C₂H₅ | 172 (S ⇌ N); 176 (N ⇌ I) |
| 5 | n-C₃H₇— | cyclohexene | cyclohexane (H) | cyclohexane (H) | —CH₃ | 148 (S ⇌ N); 149 (N ⇌ I) |
| 6 | n-C₃H₇— | cyclohexane (H) | cyclohexene | cyclohexane (H) | —CH₃ | 136 (S ⇌ I) |

Note:
S represents a smectic phase, N represents a nematic phase and I represents an isotropic liquid phase.

Each compound shown in Table 1 shows a smectic phase at room temperature.

The compound (I) of the present invention is a smectic or nematic liquid crystal compound having a weak negative dielectric anisotropy. Thus it may be mixed with other nematic liquid crystal compound(s) having a negative dielectric anisotropy and applied for a dynamic scattering mode display cell. Alternately, it may be mixed with other nematic liquid crystal compound(s) having a positive dielectric anisotropy and applied for a material for a field effect mode display cell.

Typical examples of the compounds to be mixed with the compound (I) as described above include, for example, 4-substituted benzoic acid 4'-substituted phenyl esters, 4-substituted cyclohexane carboxylic acid 4'-substituted phenyl esters, 4-substituted cyclohexanecarboxylic acid 4'-substituted biphenyl esters, 4-(4-substituted cyclohexane carbonyloxy)benzoic acid 4'-substituted phenyl esters, 4-(4-substituted cyclohexyl)benzoic acid 4'-phenyl esters, 4-(4-substituted cyclohexyl)benzoic acid 4'-substituted cyclohexyl esters, 4-substituted 4'-substituted biphenyls, 4-substituted phenyl-4'-substituted cyclohexanes, 4-substituted 4''-substituted terphenyls, 4-substituted biphenyl 4'-substituted cyclohexanes and 2-(4'-substituted phenyl)-5-substituted pyrimidines.

Table 2 shows the N-I point and Δn value of a mixed liquid crystals (A) which is widely employed in practice as matrix liquid crystals; those of mixed liquid crystals (B) comprising 80% by weight of said mixed liquid crystals (A), 10% by weight of the compound No. 1 as shown in Table 1 and 10% by weight of the compound No. 2; those of mixed liquid crystals (C) comprising 80% by weight of the mixed liquid crystals (A), 10% by weight of the compound No. 3 and 10% by weight of the compound No. 4; and those of mixed liquid crystals (D), which are employed for comparison, comprising 80% by weight of the mixed liquid crystals (A) and 20% by weight of a compound of the following formula:

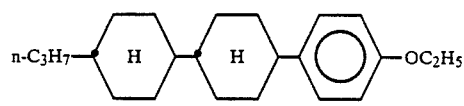

which is described in U.S. Pat. No. 4,422.951 and similar to the compounds No. 1 to No. 4 in structure.

The mixed liquid crystals (A) comprises:

20% by weight of 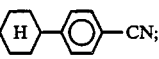

16% by weight of 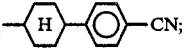

16% by weight of 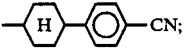

8% by weight of 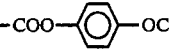

8% by weight of 

8% by weight of 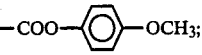

8% by weight of 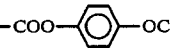

8% by weight of 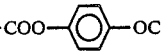 and

8% by weight of 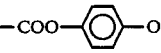

TABLE 2

| Mixed liquid crystals | N-I point (°C.) | Δn |
| --- | --- | --- |
| (A) | 54.5 | 0.0935 |
| (B) | 71.3 | 0.0909 |
| (C) | 70.3 | 0.0909 |
| (D) | 79.5 | 0.0970 |

As table 2 indicates, the compound (I) lowers the n of the mixed liquid crystals (A) and remarkably elevates the N-I point thereof, while the compound similar to it in structure remarkably elevates the N-I point of the mixed liquid crystals (A) and elevates the n thereof.

The present invention is now illustrated in greater detail by reference to the following non-limiting examples. Unless otherwise indicated, all percent and ratio are by weight.

EXAMPLE 1

30.0 g (0.126 mol) of a compound represented by the formula:

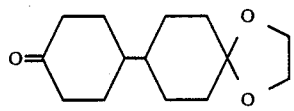

was dissolved in a mixture of 60 ml of THF and 30 ml of ethanol. To the obtained solution, was added 2.4 g (0.063 mol) of sodium borohydride in portion under stirring and cooling. Then the obtained mixture was allowed to react at room temperature for 2 hours. The reaction mixture was poured into an ice-cooled saturated aqueous solution of ammonium chloride and the reaction product thus formed was extracted with toluene. The extract was washed with water and dried.

After evaporation of the solvent, 30.0 g of a crude product containing the following compound was obtained.

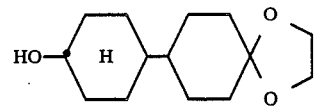

30.0 g of this crude product was dissolved in 150 ml of absolute THF. The obtained solution was added dropwise to 150 ml of a suspension of 15 g (0.31 mol) of 50% sodium hydride and 48 g (0.31 mol) of ethyl iodide in absolute THF at the reflux temperature. Then the mixture was allowed to react at this temperature for 8 hours. After cooling, the reaction mixture was poured into cold water and the reaction product thus formed was extracted with toluene. The extract was washed with water and dried. After evaporation of the solvent, 38.7 g of a crude product containing the following compound was obtained.

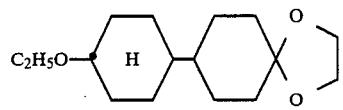

38.7 g of this crude compound was dissolved in 80 ml of toluene and 80 ml of 10% sulfuric acid was added thereto. The mixture was allowed to react under refluxing and stirring for 4 hours. After the completion of the reaction, the reaction mixture was cooled and the toluene phase was successively washed with a saturated aqueous solution of sodium hydrogencarboante and a saturated aqueous solution of common salt. After dried and evaporation of the toluene, the crude product thus obtained was purified by recrystallization from n-hexane. Thus 19.8 g (0.088 mol) of the following compound was obtained (yield: 70%).

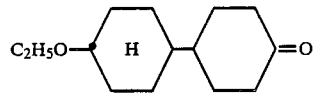

m.p.: 45–46° C.

Next, 3.0 g (0.019 mol) of a compound of the formula:

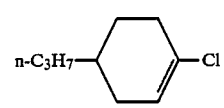

was dissolved in 9 ml of absolute diethyl ether. Then 0.26 g (0.038 gram atom) of lithium was added to the resulting solution. The obtained mixture was allowed to react under stirring at reflux temperature for 4 hours. After the completion of the reaction, the reaction mixture was cooled and 11 ml of a solution of 3.5 g (0.016 mol) of the compound of the formula:

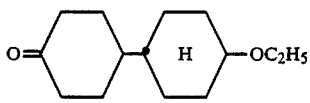

obtained above in absolute diethyl ether was added dropwise thereto at −13 to −2° C. Then the obtained mixture was allowed to react at room temperature for 30 minutes. Next, the reaction mixture was added to cold water and the reaction product thus formed was extracted with toluene. The extract was washed with water and dried. After evaporation of the solvent, 5.2 g of a crude product containing the following compound was obtained:

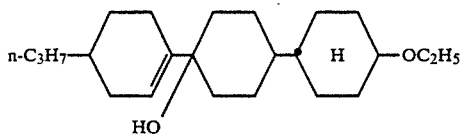

Next, 8.4 g (0.056 mol) of sodium iodide was dissolved in 35 ml of acetonitrile and 6.1 g (0.056 mol) of chlorotrimethylsilane was added dropwise thereto. To the resulting solution, was added 20 ml of a solution of the crude product obtained above in toluene under stirring at 5° to 10° C. Then the obtained mixture was allowed to react at the same temperature for 30 minutes. To the obtained reaction mixture, was added dropwise 9.7 g (0.064 mol) of DBU at 10° to 15° C. Then the obtained mixture was allowed to react at room temperature (25° C.) for 5 hours and at reflux temperature for 1 hour. The obtained reaction mixture was cooled and dilute hydrochloric acid was added thereto. The reaction product was extracted with toluene and the extract was successively washed with dilute hydrochloric aicd, a saturated aqueous solution of acidic sodium sulfite, a saturated aqueous solution of sodium hydrogencarboante and a saturated aqueous solution of common salt and then dried. After evaporation of the solvent, crude products were obtained.

These crude products were purified by chromatography on silica gel (eluent: n-hexane: toluene=1:1 by volume) and recrystallization from ethanol. Thus 2.5 g (0.0075 mol) of a mixture of the following two compounds was obtained (yield: 47%).

This mixture showed a smectic phase at room temperature and had a transparent point of 160° to 165° C.

This mixture was separated by high performance liquid chromatography and each compound thus isolated was recrystallized from ethnaol. Thus the following compounds were obtained.

Each compound showed a smectic phase at room temperature.

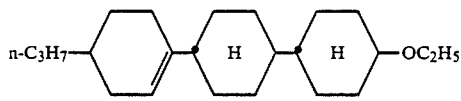

transition temperature: 174° C. (S=I); and transition temperature: 174° C. (S=I); and

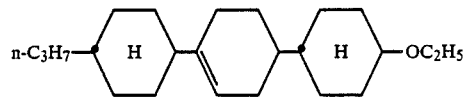

transition temperature: 158° C. (S=I).

EXAMPLE 2

The procedure of Example 1 was repeated except that 19.7 g of a compound of the formula:

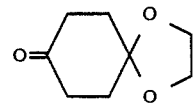

was used instead of the compound of the formula:

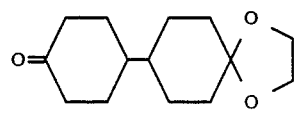

and 4.6 g of a compound of the formula:

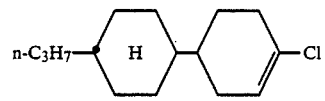

was used instead of the compound of the formula:

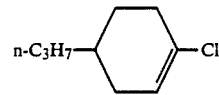

to thereby give a mixture of the following two compunds.

This mixture showed a smectic phase at room temperature and had a transparent point of 167° to 172° C.

This mixture was separated in the same manner as the one described in Example 1 and thus the following two compounds were obtained.

Each compound showed a smectic phase at room temperature.

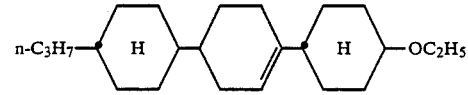

transition temperature: 156° C. (S⇌I); and

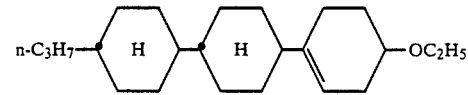

transition temperature: 172° C. (S⇌N) and 176° C. (N⇌I).

EXAMPLE 3

The procedure of Example 1 was repeated and thus a mixture of the following two compounds was obtained at a yield of 50%.

This mixture showed a smectic phase at room temperature and had a transparent point of 143° C.

The mixture was separated in the same manner as the one described in Example 1 and thus the following compounds were isolated.

Each compound showed a smectic phase at room temperature.

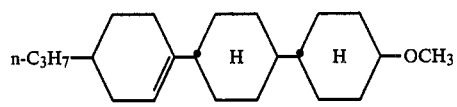

transition temperature: 148° C. (S⇌N) and
149° C. (N⇌I)

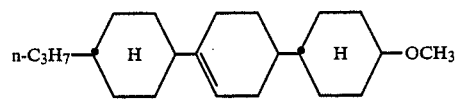

transition temperature: 136° C. (S⇌I).

The compound of the formula (I) according to the present invention is capable of lowering the Δn value of mixed liquid crystals, which have been obtained by adding said compound (I) to nematic liquid crystals widely employed as matrix liquid crystals at present, and remarkably elevating the N-I point thereof.

Therefore the compound of the formula (I) of the present invention is highly useful in the production of a liquid crystal display device excellent in visual properties and high-temperature driving.

While the invention has been described in detail and with reference to specific embodiments thereof, it will be apparent to one skilled in the art that various changes and modifications can be made therein without departing from the spirit and scope thereof.

What is claimed is:

1. A compound represented by the following general formula (I):

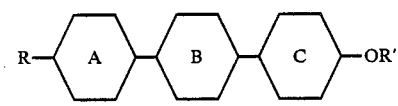

wherein R represents a straight-chain alkyl group having 1 to 9 carbon atoms; R' represents a straight-chain alkyl group having 1 to 9 carbon atoms or a trans-crotyl group; one of

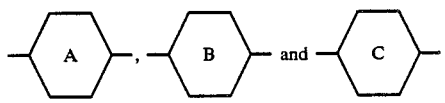

ring represents a

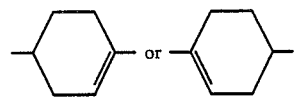

ring while other two groups represent each a

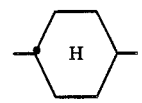

group; and the cyclohexane groups are arranged at a trans-configuration.

2. A compound as claimed in claim 1, wherein

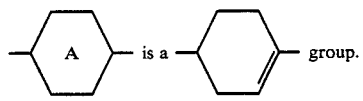

3. A compound as claimed in claim 1, wherein

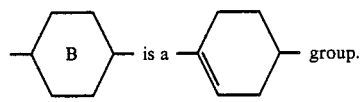

4. A compound as claimed in claim 1, wherein

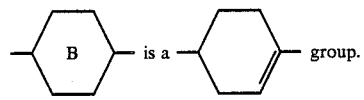

5. A compound as claimed in claim 1, wherein

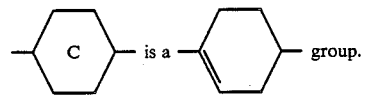

6. A compound as claimed in claim 2, wherein R is a n-propyl group and R' is a methyl group.

7. A compound as claimed in claim 2, wherein R is a n-propyl group and R' is an ethyl group.

8. A compound as claimed in claim 3, wherein R is a n-propyl group and R' is a methyl group.

9. A compound as claimed in claim 3, wherein R is a n-propyl group and R' is an ethyl group.

10. A compound as claimed in claim 4, wherein R is a n-propyl group and R' is an ethyl group.

11. A compound as claimed in claim 5, wherein R is a n-propyl group and R' is an ethyl group.

12. A nematic liquid crystal composition containing a compound as claimed in claim 1.

* * * * *